United States Patent [19]
Reichert et al.

[11] Patent Number: 5,593,677
[45] Date of Patent: *Jan. 14, 1997

[54] METHOD FOR PREVENTION OF GRAFT VERSUS HOST DISEASE

[75] Inventors: Thomas A. Reichert, Los Altos; Richard Champlin, Los Angeles, both of Calif.

[73] Assignee: Becton Dickinson and Company, Franklin Lakes, N.J.

[*] Notice: The term of this patent shall not extend beyond the expiration date of Pat. No. 5,178,858.

[21] Appl. No.: 249,651

[22] Filed: May 26, 1994

Related U.S. Application Data

[63] Continuation of Ser. No. 960,657, Oct. 14, 1992, abandoned, which is a continuation of Ser. No. 742,463, Aug. 5, 1991, Pat. No. 5,178,858, which is a continuation of Ser. No. 127,736, Dec. 21, 1987, abandoned.

[51] Int. Cl.$^6$ ............ A61K 39/395; A61K 38/13; C07K 16/38
[52] U.S. Cl. ............ 424/154.1; 424/173.1; 435/240.27; 514/11; 530/388.75
[58] Field of Search ............ 424/154.1, 173.1, 424/183.1; 435/70.21, 172.2, 240.27; 530/387.1, 388.1, 388.7, 388.75, 389.6, 391.7; 514/8, 11

[56] References Cited

FOREIGN PATENT DOCUMENTS 0235805   9/1987   European Pat. Off. ............ 39/395

OTHER PUBLICATIONS

Maranchi et al., Transplant. Int., 1:91 (1988).
Mitsuyasu et al. Ann. Int. Med., 105:20 (1986).
Henslee et al., Transplant. Proc., pp. 2701–2706 (Feb. 1987).
Leukocyte Typing III, McMichael et al. eds, pp. 932–948 (Oxgord Univ. Press, 1987).
Patterson et al., Brit. J. Hematol., 63:221 (1986).
Korngold & Sprent, Immunol. Rev., 71:5 (1983).
P. Weisz–Carrington, Princip. Clin. Immunohematol., pp. 218, 264–266 Yearbook Med. Pub. (1986).
B. Hamilton, J. Immunol., 139:2511 (1987).
Korngold & Sprent, Transplantation, 44:335 (1987).
Korngold & Sprent, Recent Adv. in Bone Marrow Transplantation, pp. 199–207, Alan R. Liss (1983).
Pals et al., J. Immuno., 132:1669 (1984).
Ferrara et al., J. Immunol. 137:1874 (1986).
R. Parkman, J. Immunol., 136:3543 (1986).
Daley et al., Blood, 70:960 (1987).
Apperley et al., Brit. J. Hematol., 69:239 (1988).
Martin et al., Blood 66:664 (1985).

*Primary Examiner*—Robert D. Budens
*Attorney, Agent, or Firm*—Royal N. Ronning, Jr.

[57] ABSTRACT

A method is disclosed for the treatment and prevention of graft versus host disease in man through the combined use of anti-CD8 monoclonal antibodies and a CD4$^+$ cell inactivator.

3 Claims, No Drawings

METHOD FOR PREVENTION OF GRAFT VERSUS HOST DISEASE

This invention was made with Government support under contract No. CA-23175 awarded by the National Institutes of Health. The Government has certain rights in this invention.

This application is a continuation of U.S. application Ser. No. 07/960,657, filed Oct. 14, 1992, now abandoned, which is a continuation of U.S. application Ser. No. 07/742,463, filed Aug. 5, 1991, now U.S. Pat. No. 5,178,858, which is a continuation of U.S. application Ser. No. 07/127,736, filed Dec. 21, 1987, now abandoned.

FIELD OF THE INVENTION

This invention relates to the prevention of or prophylaxis against graft versus host disease (GVHD), and more particularly, to the use of an anti-CD8 monoclonal antibody (MAb) together with Cyclosporine A to prevent GVHD.

BACKGROUND OF THE INVENTION

GVHD is a sometimes fatal, often debilitating complication that arises in patients who have received allogenic bone marrow transplants. Marrow transplants become necessary in the treatment of certain diseases, such as leukemia, aplastic anemia or certain genetic disorders, in which the patient's own marrow is severly flawed and where total body irradiation or chemotherapy destroy the patient's hematopoietic system. Absent reconstitution of the hematopoietic system, the patient will be severely immunodepressed and susceptible to infection. Hence GVHD is frequently encountered in bone marrow transplantation and presents a major obstacle to the successful treatment of the above disorders.

Working with the H2 histocompatability system of mice, Korngold and Sprent, Immunological Rev., 71:5 (1983), have reviewed the suspected etiology and pathology of GVHD. Briefly, in its acute form, GVHD is an extraordinarily morbid and often fatal disorder which is primarily, if not exclusively, mediated by T lymphocytes. It typically results from the incomplete immunologic matching of donor with recipient Human Leukocyte antigens (HLA). There are four major HLA antigens: the Class I HLA-A, HLA-B and HLA-C antigens; and the Class II HLA-D region antigens. These antigens form the major histocompatability complex (MHC), and are expressed in virtually all cells, including nucleated cells in the bone marrow. MHC antigens are cell surface glycoproteins expressed on the lipid membrane. These HLA antigens can trigger the immune system (principally T cells) to respond to foreign antigens. For a more detailed description of the HLA system, see P. Weisz-Carrington, Principles of Clinical Immunohematology, p. 218, YearBook Medical Publishers, Inc. (1986).

Even in those cases where the most complete HLA matching is correctly done, GVHD frequently results. It has been suggested that GVHD results, in those instance, from alloaggression due to minor histocompatability antigen differences for which many authors have suggested the depletion of donor T cells as a means to avoid GVHD.

Korngold and Sprent were the first to suggest that not all T cells, however, are necessarily involved in inducing GVHD. T cells (CD3$^+$) have two major subset populations: T helper/inducer cells (CD4$^+$) and T cytotoxic/suppressor cells (CD8$^+$). These authors suggested in 1983, on the basis of experiments with a single MHC compatible pair of mouse strains, that the CD8$^+$ subset appears to be involved in GVHD. Later, however, B. Hamilton, J. Immunol., 139:2511 (1987) and Korngold and Sprent (1987) reported on experiments in multiple strains of mice. They showed that in some strains merely by depleting T cytotoxic/suppressor cells (Lyt2$^+$ in mice) did not abolish GVHD in all mouse strains, but that depletion of L3T4$^+$ cells also was required for some strain combinations.

BRIEF DESCRIPTION OF THE INVENTION

The present invention comprises a method to prevent GVHD. The method comprises the following steps: in a patient undergoing allogenic bone marrow transplantation, marrow from an HLA-matched donor is treated with anti-CD8 monoclonal antibody to deplete the donor's marrow of T cytotoxic/suppressor cells; the treated marrow then is transplanted into the patient; and a CD4$^+$ cell inactivator, such as Cyclosporine A, is given to the patient.

DETAILED DESCRIPTION OF THE INVENTION

Patients with either acute myelogenous leukemia (AML), acute lymphoblastic leukemia (ALL) or chronic granulocytic leukemia (CGL) were considered for bone marrow transplantation as part of their therapy. Patients were selected for treatment if they had an HLA A, B and D matched donor. Patients with other types of diseases and with other HLA pairings also may be considered for treatment.

Prior to transplantation, each patient underwent a conditioning regime. The conditioning regime is designed to destroy all malignant cells in the patient. This regime followed standard procedures and included total body irradiation and treatment with anti-neoplastic agents, such as cyclophosphamide (Bristol-Meyers Laboratories) or cytarabine ("ARA-C", UpJohn) and mitoxantrone (Lederle Laboratories). Each type of disease may have a slightly different conditioning regime and care should must be taken to ensure that the proper regime is followed; however, so long as standard pretreatment procedures are employed, the specific conditioning regime is not critical to the practice of the invention. For a review of leukemia conditioning regimes prior to bone marrow transplantation, see Weisz-Carrington, pp. 264–266.

While the patient was undergoing the conditioning regime, bone marrow from the HLA-matched donor was aspirated from the iliac crests. Approximately 3–5 ×10$^8$ nucleated marrow cells/kg donor body weight typically were obtained. Mononuclear cells were obtained by Ficoll-Hypaque (Pharmacia) density dependent centrifugation. Mononuclear cells then were suspended in 10% McCoy's medium (American Scientific Products) with 10% patient serum to a concentration of 2×10$^7$ cells/ml. To the mixture of suspended cells and patient serum was added an amount of an anti-CD8 $^+$monoclonal antibody sufficient to deplete the CD8$^+$ in the donor's bone marrow. In this example, 10 ug/ml of MAb was used. The antibody may be selected from the group consisting of Anti-Leu-2b (available from Becton Dickinson Immunocytometry Systems), Anti-Leu-2c (deposited in the laboratory of Dr. David Buck, Becton Dickinson Immunocytometry Systems, as clone L55), OKT8 (available from Ortho Diagnostics, Inc.) or a plurality of such cytotoxic CD8$^+$ antibodies. The preferred cytotoxic CD8$^+$ monoclonal antibody is Anti-Leu-2c.

After 30 minutes, the monoclonal antibody treated cells were washed and resuspended in newborn rabbit complement (Pel-Freeze Biologicals) at 37° C for 45 minutes. The cells then were washed and resuspended in RPMI 1640 (GIBCO), and were placed in a transfusion bag ready for transplantation.

Treatment with anti-CD8 antibody and complement may be repeated to ensure that the $CD8^+T$ cells have been depleted. Depletion of the T cells may be checked by immunophenotyping various T cell subsets pre- and post-depletion. This may be done, for example, by using flow cytometry and fluorescently labeled MAbs.

It will be appreciated by those skilled in the art that the anti-CD8 MAb need not be cytotoxic in order to deplete the donor's bone marrow of $CD8^+$cells. A non-cytotoxic anti-CD8 Mab may be linked to a solid phase immunoabsorbant, such as polystyrene beads. The marrow then is passed over the immunoabsorbant to deplete the $CD8^+$cells. Anti-Leu-2a (available from Becton Dickinson Immunocytometry Systems) is one such antibody. Similarly, it will be appreciated that the treatment of the donor's marrow to deplete the $CD8^+$cells may comprise use of an effective amount of a cytotoxic $CD8^+$agent and immunoabsorbation with a $CD8^+$ agent. In all cases, the critical element is to deplete the donor's bone marrow of $CD8^+$cells.

Bone marrow cells prepared as above then were transplanted into a conditioned patient. Cells typically were administered I/V over 60–120 minutes. Patients were pre-medicated with acetominophen (or similar fever depressing drugs) and steroids (such as hydrocortisone). These medications were given to patients to prevent hypersensitivity reactions.

Following transplantation, patients were kept in protective isolation until the absolute granulocyte returned to acceptable levels.

A $CD4^+$cell inactivator then was given. In this example, Cyclosporine A (Sandoz) was given I/V prior to transplantation and continued daily for the next six months to block the function of $CD4^+$cells. Initial doses may be in the range of 2 to 8 mg/kg/day I/V, 3.0 mg/kg was considered optimal, for the first twenty-one days, although dosages were reduced for patients over 35. Patients were switched to oral doses of the same amount for the next three months. The dose then was titered approximately 5% per week until a level of 100 mg/day was achieved. Other cytotoxic $CD4^+$agents such as anti-CD4 MAbs (e.g., Anti-Leu-3a, Becton Dickinson Immunocytometry Systems) may be substituted for Cyclosporine A; however, in all cases, standard procedures should be followed in monitoring a patient's vital and other functions during treatment.

Monoclonal antibody treated bone marrow was examined for T cell depletion. Fluourescein isothiocyanate (FITC) and phycoerythrin (PE) conjugated antibodies (e.g, Anti-Leu-4 and Anti-Leu-2b, respectively) were used to measure T cell ($CD8^+$) depletion using standard two color flow cytometric analysis on a FACStar™ flow cytometer (Becton Dickinson Immunocytometry Systems). $CD8^+$cells were reduced to less than 1% of the population of transplanted cells in 14 patients.

Of these 14 patients, two developed grade 2 (cutenous) acute GVHD and one developed grade 3 (rash and diarrhea) acute GVHD. All three patients recovered within 48 hours upon administration of corticosteroids. No deaths from GVHD have been seen. All patients showed sustained engraftment, at the immunologic reconstruction of the patient's hematopoietic system was notable for its balanced recovery of $CD4^+/CD8^+$cells.

Variations and modifications of the above method may suggest themselves to those skilled in the art. Accordingly, the foregoing description should not be taken in a limiting sense.

What is claimed is:

1. A method for prevention of or prophylaxis against GVHD in a patient to undergo a bone marrow transplant, where bone marrow of an allogenic donor has been matched to the patient for HLA compatibility, comprising the steps of treating the bone marrow of the donor with one or more anti-CD8 monoclonal antibodies and complement in an amount sufficient to deplete T cytotoxic/suppressor cells to less than 1%, transplanting the treated bone marrow to the patient, and administering to the patient an effective amount of Cyclosporine A sufficient to inactivate $CD4^+$ cells.

2. The method of claim 1 wherein the anti-CD8 monoclonal antibodies are functionally equivalent to the monoclonal antibody produced by the hybridoma deposited as ATCC HB 9918.

3. The method of claim 1 wherein the anti-CD8 monoclonal antibody further comprises a plurality of anti-CD8 monoclonal antibodies.

* * * * *